United States Patent [19]
Donnelly et al.

[11] Patent Number: 6,159,738
[45] Date of Patent: Dec. 12, 2000

[54] METHOD FOR CONSTRUCTION OF BACTERIAL STRAINS WITH INCREASED SUCCINIC ACID PRODUCTION

[75] Inventors: Mark I. Donnelly, Warrenville; Cynthia Sanville-Millard, Plainfield; Ranjini Chatterjee, Park Ridge, all of Ill.

[73] Assignee: University of Chicago, Chicago, Ill.

[21] Appl. No.: 09/067,931

[22] Filed: Apr. 28, 1998

[51] Int. Cl.$^7$ .................................. C12P 7/46; C12P 7/00; C12N 15/74; C12N 15/00

[52] U.S. Cl. ....................... 435/471; 435/140; 435/252.3; 435/252.31; 435/252.33; 435/252.9; 435/440; 435/145; 435/472; 536/23.2; 536/23.1; 536/23.7

[58] Field of Search ................................ 435/145, 252.3, 435/471, 140, 252.31, 252.33, 252.9, 440, 472; 536/23.2, 23.1, 23.7

[56] References Cited

PUBLICATIONS

Postma et al., Phosphoenolpyruvate Carbohydrate Phosphotransferase Systems of Bacteria, Micro. Rev. 57(3): 543–594, Sep. 1993.

*Primary Examiner*—Rebecca E. Prouty
*Assistant Examiner*—Richard Hutson
*Attorney, Agent, or Firm*—Cherskov & Flaynik

[57] ABSTRACT

A fermentation process for producing succinic acid is provided comprising selecting a bacterial strain that does not produce succinic acid in high yield, disrupting the normal regulation of sugar metabolism of said bacterial strain, and combining the mutant bacterial strain and selected sugar in anaerobic conditions to facilitate production of succinic acid. Also provided is a method for changing low yield succinic acid producing bacteria to high yield succinic acid producing bacteria comprising selecting a bacterial strain having a phosphotransferase system and altering the phosphotransferase system so as to allow the bacterial strain to simultaneously metabolize different sugars.

9 Claims, 3 Drawing Sheets circles - glucose
squares - succinic acid
diamonds - acetic acid
x's - ethanol

Metabolism of glucose and xylose to succinic acid by AFP111

METHOD FOR CONSTRUCTION OF BACTERIAL STRAINS WITH INCREASED SUCCINIC ACID PRODUCTION

CONTRACTUAL ORIGIN OF THE INVENTION

The U.S. Government has rights in this invention under Contract No. W-31-109-ENG-38 between the U.S. Department of Energy and the University of Chicago representing Argonne National Laboratory.

BACKGROUND OF THE INVENTION

1. Field of the Invention

This invention relates to a fermentation method to produce succinic acid, and more particularly this invention relates to a method for creating bacterial strains capable of utilizing a myriad of sugars to produce succinic acid as a major fermentation product.

2. Background of the Invention

Carboxylic acids hold promise as potential precursors for numerous chemicals. For example, succinic acid can serve as a feedstock for such plastic precursors as 1,4-butanediol (BDO), tetrahydrofuran, and gamma-butyrolactone. New products derived from succinic acid are under development, with the most notable of these being polyester which is made by linking succinic acid and BDO. Generally, esters of succinic acids have the potential of being new, "green" solvents that can supplant more harmful solvents. In total, succinic acid could serve as a precursor for millions of pounds of chemicals annually at a total market value of over $1 billion. Along with succinic acid, other 4-carbon dicarboxylic acids, such as malic acid, and fumaric acid also have feedstock potential.

The production of these carboxylic acids from renewable feedstocks (in this case through fermentation processes) is an avenue to supplant the more energy intensive methods of deriving such acids from nonrenewable sources.

Succinate is an intermediate for anaerobic fermentations by propionate-producing bacteria but those processes result in low yields and concentrations.

Anaerobic rumen bacteria, such as *Bacteroides ruminicola* and *Bacteroides amylophilus* also produce succinate. However, rumen organisms are characteristically unstable in fermentation processes.

It has long been known that a mixture of acids are produced from *E. coli* fermentation, as elaborated in Stokes, J. L. 1949 "Fermentation of glucose by suspensions of *Escherichia coli*" *J. Bacteriol.* 57:147–158. However, for each mole of glucose fermented, only 1.2 moles of formic acid, 0.1–0.2 moles of lactic acid, and 0.3–0.4 moles of succinic acid are produced. As such, efforts to produce carboxylic acids fermentatively have resulted in relatively large amounts of growth substrates, such as glucose, not being converted to desired product.

Some bacteria, such as *A. succiniciproducens*, utilized in fermentation processes as outlined in U.S. Pat. No. 5,143,834 to Glassner et al., naturally produce succinic acid in moderate titers up to only about 35–40 grams per liter (g/L). The *A. succiniciproducens* host strain has been shown to be not highly osmotolerant in that it does not tolerate high concentrations of salts and is further inhibited by moderate concentrations of product. Lastly, *A. succiniciproducens* presents handling problems in that as an obligate anaerobe, procedures using the organism must be done in the absence of oxygen. Also, medium preparation for the inoculum requires the addition of tryptophan and also requires the addition of a solution of cysteine, HCl, and sodium sulfide which contains corrosive and toxic $H_2S$.

Previous efforts by the inventors to produce succinic acid has resulted in the isolation and utilization of a mutant bacterium. The mutant, available as ATCC accession number 202021, is the subject of U.S. patent application Ser. No. 08/556,805 to the instant Assignee. U.S. application Ser. No. 08/556,805, incorporated herein by reference, teaches a succinic acid-producing bacterial strain (AFP 111) which spontaneously mutates from its precursor. The mutant is able to grow fermentatively on glucose to produce succinic acid in high yields, while its precursor is unable to do so. However, an obvious drawback to utilizing this method of succinic acid production is its limitation to a single mutant organism.

None of the prior attempts outlined supra have resulted in a process for feeding a myriad of feedstocks to several different metabolizing organisms to produce high quantities of succinic acid. Such flexibility in types of nutrients and organisms utilized would result in exploiting the lower costs of many feedstocks, such as corn stover, logging slash, and other lignocellulosic feedstocks, and the higher product tolerances and robust metabolisms of certain organisms.

A need exists in the art for a fermentation process whereby a myriad of feedstocks can be fed to several different metabolizing organisms to produce large quantities of succinic acid. The process should utilize low cost nutrients, and perhaps different organisms to facilitate fermentation in various environments. The process should also yield molar ratios of approximately 1:1 product-to-growth substrate.

SUMMARY OF THE INVENTION

It is an object of the present invention to provide a method for producing succinic acid that overcomes many of the disadvantages of the prior art.

It is another object of the present invention to provide a fermentation process that produces high yields of succinic acid. A feature of the invention is the utilization of a mutant gene in otherwise-intact bacterial genomes. An advantage of the invention is the alteration of the genomes of bacteria, which do not produce succinic acid in high yield, to create bacteria which produce primarily succinic acid, wherein a myriad of feedstocks are simultaneously utilized by the now-altered host bacteria.

Still another object of the present invention is to provide a process for manipulating bacteria to produce large amounts of succinic acid. A feature of the invention is the disruption of the normal regulation of sugar metabolism in the bacteria. An advantage of the invention is the ability to manipulate a variety of bacteria to facilitate relatively high product-to-growth substrate ratios (i.e., at or above 1:1) in fermentation processes for producing succinic acid. Another advantage of the invention is the ability to utilize bacteria which are glucose metabolisers and non-glucose metabolisers.

Yet another object of the present invention is the utilization of a mutant gene to shut down catabolite repression processes. A feature of the invention is the homologous recombination of the mutant gene into the recipient chromosome of a selected bacteria. An advantage of the invention is a bacteria with its catabolite repression mechanism turned off so that both glucose and non-glucose can be utilized to produce succinic acid.

Briefly, the invention provides a fermentation process for producing succinic acid in at least a 1:1 product to sugar ratio, comprising selecting a bacterial strain incapable producing succinic acid in high yield; disrupting the normal regulation of sugar metabolism of said bacterial strain; and combining the mutant bacterial strain and selected sugar in anaerobic conditions to facilitate production of succinic acid.

The invention also provides a method for changing fermentative bacteria which may produce no succinic acid or low amounts of succinic acid into ones which produce primarily succinic acid comprising selecting a bacterial strain having a phosphotransferase system, and altering the phosphotransferase system so as to allow the bacterial strain to simultaneously metabolize different sugars to succinic acid in high yield.

The invention further provides a nucleotide mutation for altering genomes of fermentative bacteria to produce bacteria capable of producing succinic acid in at least a product-to-sugar feedstock molar ratio of 1:1.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

The inventors have found a method for converting a variety of bacteria to high yield succinic acid producers. For example, the method can be utilized to convert fermentative bacteria having no or low succinic acid product yields (i.e., less than 0.5 moles per one mole of fed growth substrate), to bacteria having high succinic acid product yields (i.e., greater than or equal to 1 mole of succinic acid per one more of fed growth substrate). The method turns off catabolite repression mechanisms present in bacteria so as to allow the bacteria to produce succinic acid using glucose and non-glucose feedstocks.

The inventors have found that inasmuch as the fermentation metabolic pathway to succinic acid formation in bacteria appears to be subject to catabolite repression in the presence of a functional phosphotransferase gene (ptsG), a mutant in the gene results in increased flux through the metabolic pathway of the bacteria to succinic acid.

To delineate the novel pathway to succinic acid production, the mutation was first mapped using classical genetic methods. Regions of the *E. coli* chromosome that encoded components of the phosphotransferase system (PTS) were targeted in the mapping. The mutation was mapped to the ptsG locus at 24.96 minutes (min) on the chromosome. The inventors surmise that a mutation in ptsG may de-repress the pathway directly by altering the phosphorylation state of one or more proteins of the PTS. Alternatively, or in addition, the mutant may de-repress the pathway indirectly by altering glucose- and other metabolite-concentrations in the cell, subsequently allowing cells to grow fermentatively through formation of succinic acid.

Figure 1:
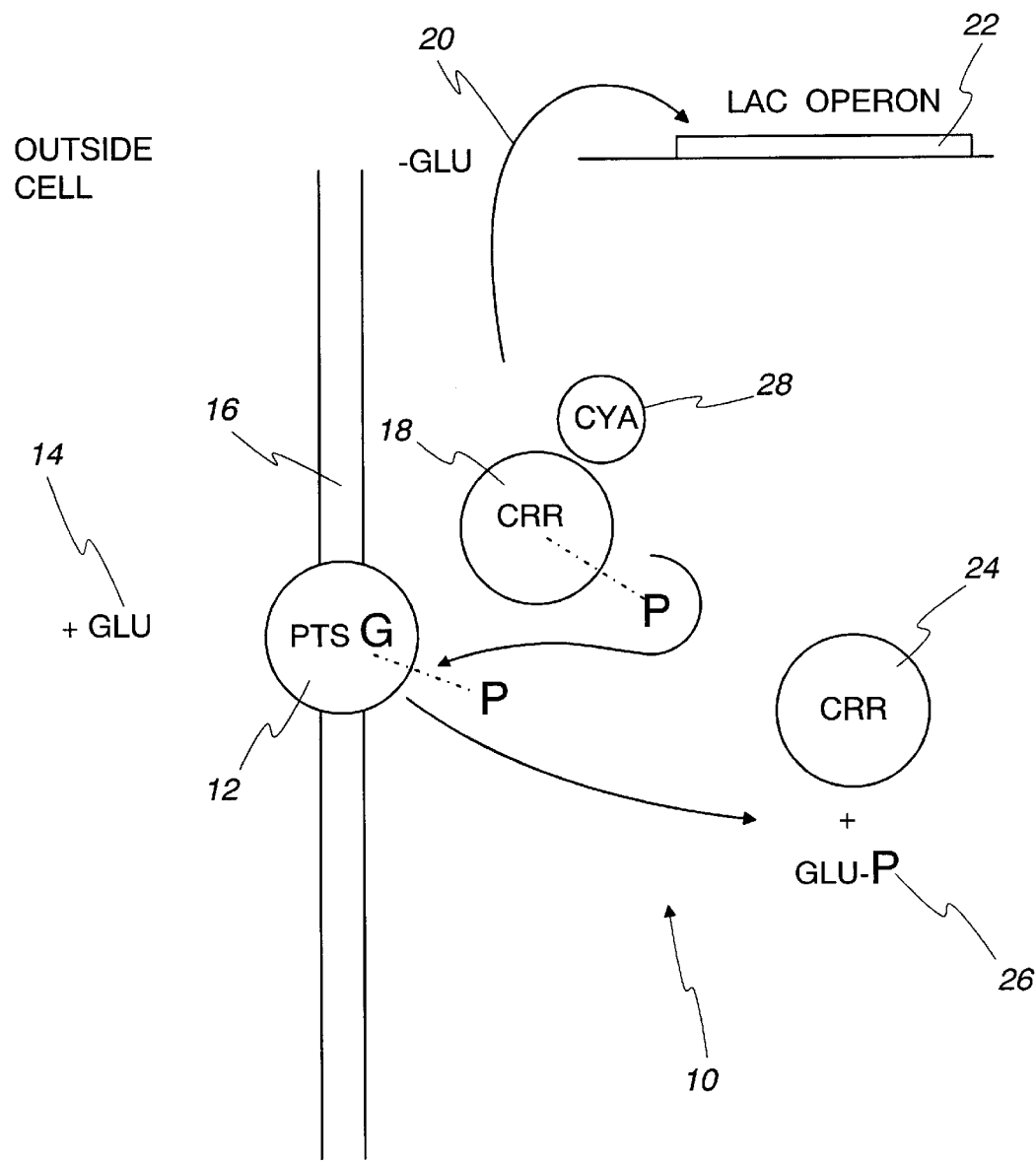
FIG. 1 is a schematic diagram of a catabolite repression mechanism in bacteria, in accordance with features of the present invention.

A schematic diagram of the targeted catabolite repression mechanism is depicted as numeral 10 in FIG. 1. The ptsG gene 12 is a glucose uptake protein that, in the presence of glucose 14 stops the use by the bacteria of non-glucose sugars. The ptsG gene encodes the cell membrane 16 component of the glucose-specific phosphenolpyruvate:glucose phosphotransferase system. An intact ptsG gene takes up and phosphorylates glucose, and causes phosphate to cleave from the catabolite repression release (crr) protein 18. At this juncture, crr-P converts to its deactivated (dephosphorylated) form crr 24, thereby causing a deactivation of the mechanism 20 for utilizing non-glucose sugars. For example, and as depicted in FIG. 1, in the absence of crr-P, activation of a lactose operon 22 would not occur. Instead, the cleaved phosphate from the crr-P is found on the glucose metabolite glucose-6-phosphate, 26.

Conversely, in the absence of glucose, the crr protein 18 stays intact, inasmuch as its phosphate is not lost, and alternate sugars are subsequently utilized. For example, as depicted in FIG. 1, the intact crr protein would, in conjunction with adenylate cyclase (cya) 28, activate a lactose operon 22 to utilize any lactose contained in a feed mixture.

The inventors have found that a mutant of the ptsG protein is responsible for the wide utility of the succinic acid producing bacterium (AFP 111) disclosed in U.S. patent application Ser. No. 08/556,805, discussed supra. Specifically, by inserting the mutant into various bacteria, the inventors have stifled normal catabolite repression so as to allow utilization of both glucose and non-glucose feedstocks by the same bacteria to provide high stoichiometric yields of succinic acid. Molar ratios of product to substrate as high as 1.3:1 have been obtained..

As explained in greater detail below, the efficacy of the mutant was shown by transforming AFP 111's parent bacteria NZN 111, which has an intact catabolite repression mechanism, into a bacteria having a disabled catabolite repression mechanism. NZN 111 is unable to grow fermentatively on glucose, inasmuch as its ability to convert pyruvate to acetylCoA or to lactate is disrupted due to inactivation of pflAB and ldhA, which are the genes encoding pyruvate:formate lyase and the fermentative lactate dehydrogenase, respectively.

Two phenotypic characteristics conferred by the spontaneous mutation in AFP 111 that distinguish it from its immediate precursor NZN 111 (W1485,pfl;;Cam, ldhA::Kan) are its ability to ferment glucose to succinic acid, acetic acid and ethanol in a 2:1:1 stoichiometry, and loss of catabolite repression. Both characteristics also were exhibited by a series of 13 other chromosomal mutants (AFP 112–124) that arose from NZN 111 when selected for anaerobic growth on glucose. These data indicate that the mutant ptsG could be reproducibly selected from NZN 111.

The ability of a plasmid-encoded, functional ptsG gene to reverse the phenotype of AFP 111 and co-spontaneous mutants AFP 112–124 was also examined.

Plasmid PCB10, which contains a functional ptsG gene, was introduced into AFP 111 and four transformants were analyzed. The plasmid restored normal catabolite repression and eliminated the ability to grow fermentatively on glucose, indicating that the presence of a functional ptsG gene eliminated the AFP 111 phenotype.

The mutation was shown to be the same on all spontaneous mutants (AFP 111–124) by introduction of a functional ptsG gene by bacteriophage P1 transduction.

Transductants were screened for restoration of normal catabolite repression based on the formation of white colonies on x-gal/lactose/glucose agar. None of the selected transductants were able to grow fermentatively on glucose. Introduction of a functional ptsG gene reverted their phenotype to that of NZN 111.

Any bacterium able to make any succinic acid fermentatively are particularly suitable transduction candidates, including but not limited to gram-negative and gram-positive fermentative bacteria. Preferably, suitable strains include but are not limited to *E. coli,* Klebsiella, Erwinia, and Lactobacillus. Those *E. coli* strains listed in Table 1, infra are particularly noteworthy as transduction candidates.

TABLE 1

*E. coli* Strains Suitable for Transduction

| Strain | Relevent genotype | Source and/or reference |
|---|---|---|
| W1485 | F⁺ wild type, λ⁻, rpoS396(Am), rph-1 | CGSC 5024[1] |
| FMJ123 | W1485, ΔpflAB::Cam | [2] |
| LS1 | W1485, ldhA::Kan | [3] |
| NZN111 | W1485, ldhA::Kan, ΔpflAB::Cam | [2] |
| AFP111 | NZN111, afp | Spontaneous mutant of NZN111; (9) |
| AFP112–124 | NZN111, afp | Spontaneous mutants; this study |
| BW6156 | λ⁻, relA1, spoT1, metB1, zje-2005::Tn10 | CGSC 6754 |
| BW6159 | λ⁻, relA1, spoT1, ilv-691::Tn10, thi-1 | CGSC 6755 |
| BW7623 | purK79::Tn10, λ⁻, relA, spoT1 | CGSC 6815 |
| CAG12078 | λ⁻, zce-726::Tn10, rph-1 | CGSC 7361 |
| CAG18463 | λ⁻, zcf-117::Tn10, rph-1 | CGSC 7363 |
| CAG18468 | λ⁻, nupC510::Tn10, rph-1 | CGSC 7410 |
| CAG18470 | λ⁻, purC80::Tn10, rph-1 | CGSC 7413 |
| LA-12G | λ⁻, ptsG21, relA1, spoT1, thi-1 | CGSC 5085 |
| AFP301–307 | pfl::Cam, ldh::Kan, zce-726::Tn10 | P1(CAG12078) X AFP111; this study |
| RC308 | LA-12G, zce-726::Tn10 (ptsG21) | P1(CAG12078) X LA-12G; this study |
| AFP310–313 | NZN111, ptsG21, zce-726::Tn10 | P1(RC308) X NZN111; this study |
| AFP165 | W1485, ptsG21, zce-726::Tn10 | P1(RC308) X W1485; this study |
| AFP166 | FMJ123, ptsG21, zce-726::Tn10 | P1(RC308) X FMJ123; this study |
| AFP167 | LS1, ptsG21, zce-726::Tn10 | P1(RC308) X LS1; this study |

[1] CGSC = Coli Genetic Stock Center, Yale University.
[2] As disclosed in Bunch, P. K. et al. "The ldhA gene encoding the fermentative lactate dehydrogenase of *E. coli*." Microb. 143:187–195.
[3] As disclosed in Stols, L. et al. "Production of succinic acid through overexpression of NAD⁺ - dependent malic enzyme in an *E. coli* mutant." Appl. Environ. Microbiol. 63:2695–2701

Detail of Transduction of Normal Bacteria

To establish that a single mutation in the ptsG gene was sufficient for the phenotypic traits of AFP 111, a known defective pstG gene was transduced into NZN 111. Specifically, strain LA-12G (Coli Genetic Stock Center #5085, ptsG21) was selected as the source of the mutant. In order to position a selectable marker near the defective ptsG gene, the zce::Tn10 (insertion at 24.6 min) from strain CAG12078 was transduced into LA-12G by bacteriophage P1 transduction. Transposon 10 (Tn 10) is a particularly suitable transposable element given its association with a tetracycline resistance marker. A transductant (designated RC308) selected from this cross, based on both its resistance to tetracycline and its lack of catabolite repression, was subsequently used as the P1 donor strain for transduction of the mutant ptsG gene into the recipient NZN 111.

Transductants from the P1 (RC308) X NZN111 cross were selected for resistance to tetracycline and kanamycin to select for NZN 111, and screened for the formation of blue colonies on X-gal/lactose/glucose agar (the latter trait indicating the presence of the mutant ptsG gene). Cotransduction of the mutant ptsG gene with the zce::TN10 marker occurred with a frequency of 76 percent.

Figure 2:
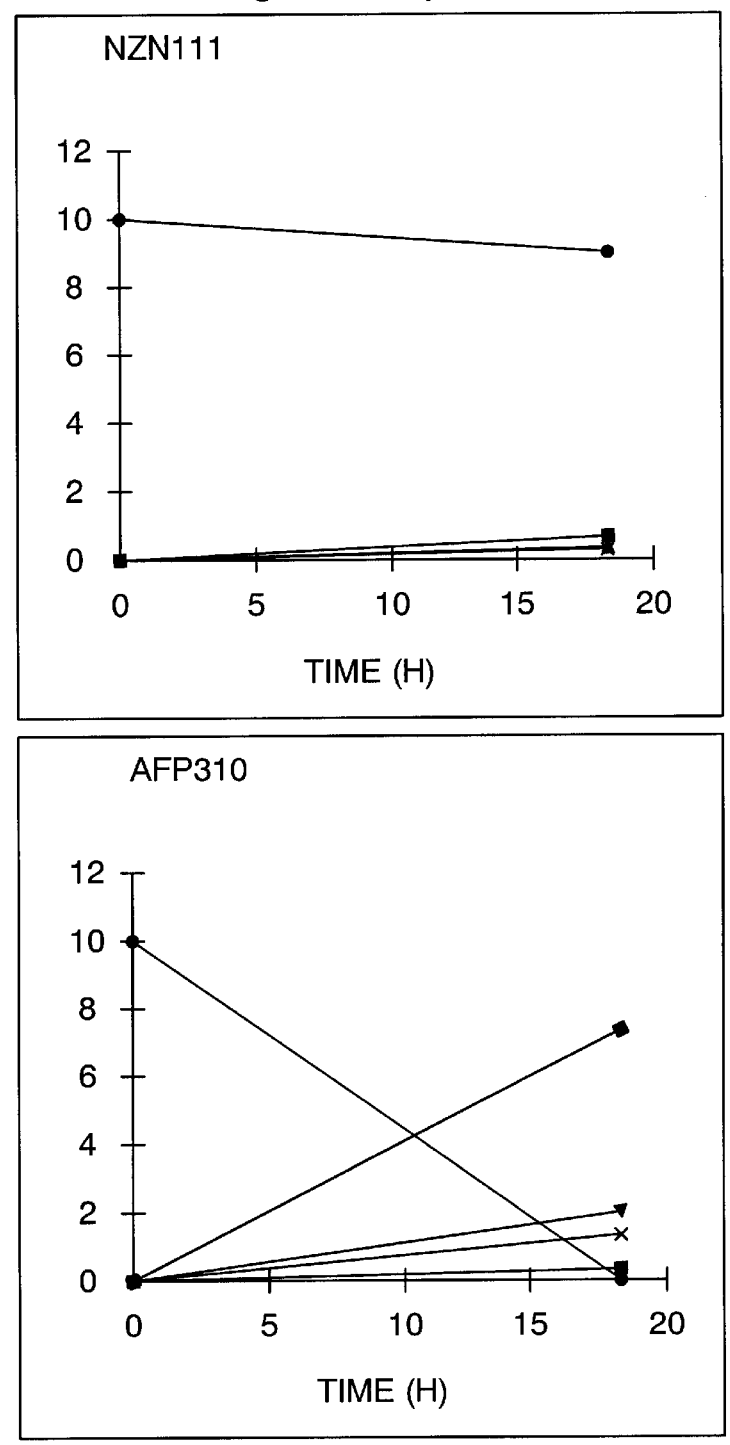
FIG. 2 is a graph depicting an enhanced production of succinic acid after transformation of a bacteria with a mutant gene, in accordance with features of the present invention.

Four blue transductants (designated AFP 310–313) were chosen at random and analyzed for fermentative metabolism. As is depicted in Table 2, infra, strains AFP 310–313 fermented glucose to a mixture of succinic acid, acetic acid and ethanol. However, succinic acid constituted the major product, in similar fashion to that seen with AFP 111. Specifically, succinic acid yields are more than three-times the yields of acetic acid and ethanol by weight. This high succinic acid yield is further depicted in FIG. 2. FIG. 2 illustrates that when non-glucose-metabolising NZN 111 is transformed with the ptsG gene mutant, the new bacteria AFP 310 results that displays a dramatic ability to digest glucose to produce succinic acid. The presence of other compounds, such as acetic acid and ethanol is also indicated.

TABLE 2

Creation of the AFP111 phenotype by introduction of a mutant ptsG gene into NZN111

| Strains[a] | Source[b] | Catabolite repression[c] | Glucose remaining and products formed (g/L)[d] | | | | | |
|---|---|---|---|---|---|---|---|---|
| | | | Glucose | SA | AA | FA | LA | EtOH | Pyruvate |
| AFP310 | P1 (RC308) X NZN111 | − | 0.00 | 7.33 | 1.98 | 0.27 | 0.00 | 1.06 | 0.002 |
| AFP311 | P1 (RC308) X NZN111 | − | 0.00 | 7.08 | 2.10 | 0.19 | 0.00 | 1.11 | 0.000 |
| AFP312 | P1 (RC308) X NZN111 | − | 0.00 | 7.17 | 2.04 | 0.16 | 0.11 | 1.06 | 0.001 |
| AFP313 | P1 (RC308) X NZN111 | − | 0.00 | 6.15 | 1.84 | 0.22 | 0.07 | 1.94 | 0.000 |
| AFP111 | pfl::Cam, ldh::Kan, afp | − | 0.17 | 6.68 | 1.70 | 0.19 | 0.00 | 0.90 | 0.005 |
| NZN111 | pfl::Cam, ldh::Kan | + | 8.98 | 0.27 | 0.10 | 0.08 | 0.00 | 0.00 | 0.097 |

[a] Strains AFP110–AFP113 were positive transductants selected at random for further characterization from the P1 (RC308) X NZN111 cross.
[b] Construction of P1 donor strain RC308 is described in the text.
[c] The presence of or absence of catabolite repression, depicted by (+) or (−), respectively, was determined by the coloration of individual colonies on X-gal-containing agar.
[d] Fermentative growth of strains and quantitation of products is described under "Growth Detail". SA = succinic acid, AA = acetic acid, FA = formic acid, LA = lactic acid and EtOH = ethanol. Eleven g/L of glucose was included in the media; glucose remaining and products formed were quantitated following 26 hours of anaerobic growth.

These data establish that the phenotype of AFP 111 is the consequence of a mutation of the ptsG gene, which encodes the PTS protein II-Bg$^{glc}$, the membrane component of the glucose transport protein.

Even precursor strains to NZN 111, which itself is the precursor to spontaneous mutant AFP 111, were transformed with the mutant ptsG gene. Strains W1485 (wild type), FMJ123 (W1485, Δpfl:AB::Cam) and LS1 (W1485, ldhA::Kan) are precursor strains in the lineage of both NZN 111 (W1485, pfl::Cam, ldhA::Kan) and AFP 111 (NZN 111, afp=ptsG). The defective ptsG21 gene from RC308 was transduced into these three strains to confirm that the AFP 111 phenotype would be generated. Transductants from each cross were selected for the appropriate antibiotic resistance markers as well as for the formation of blue colonies on X-gal/glucose agar, thereby indicating transfer of the defective ptsG21 gene. The transductants designated AFP 165, AFP 166, and AFP 167 are ptsG21 derivatives of W1485, FMJ123, and LS1, respectively.

The product distributions from glucose fermentations by the transductants AFP 165–167 are compared to their respective parent strains in Table 3, infra. As is illustrated therein, the introduction of the mutant ptsG21 gene resulted in an altered fermentation with succinic acid produced as the major product by weight.

The results in Table 3 indicate that the metabolic pathway to succinic acid production exists in other bacterial strains but is either inefficient in the presence of competing pathways or is subject to catabolite repression in the presence of a functional ptsG gene. As such, disruptions in the pflAB or ldhA genes are not essential for turning on the succinic acid metabolic pathway, rather a mutation in ptsG alone is sufficient to elicit good succinic acid yields.

Figure 3:
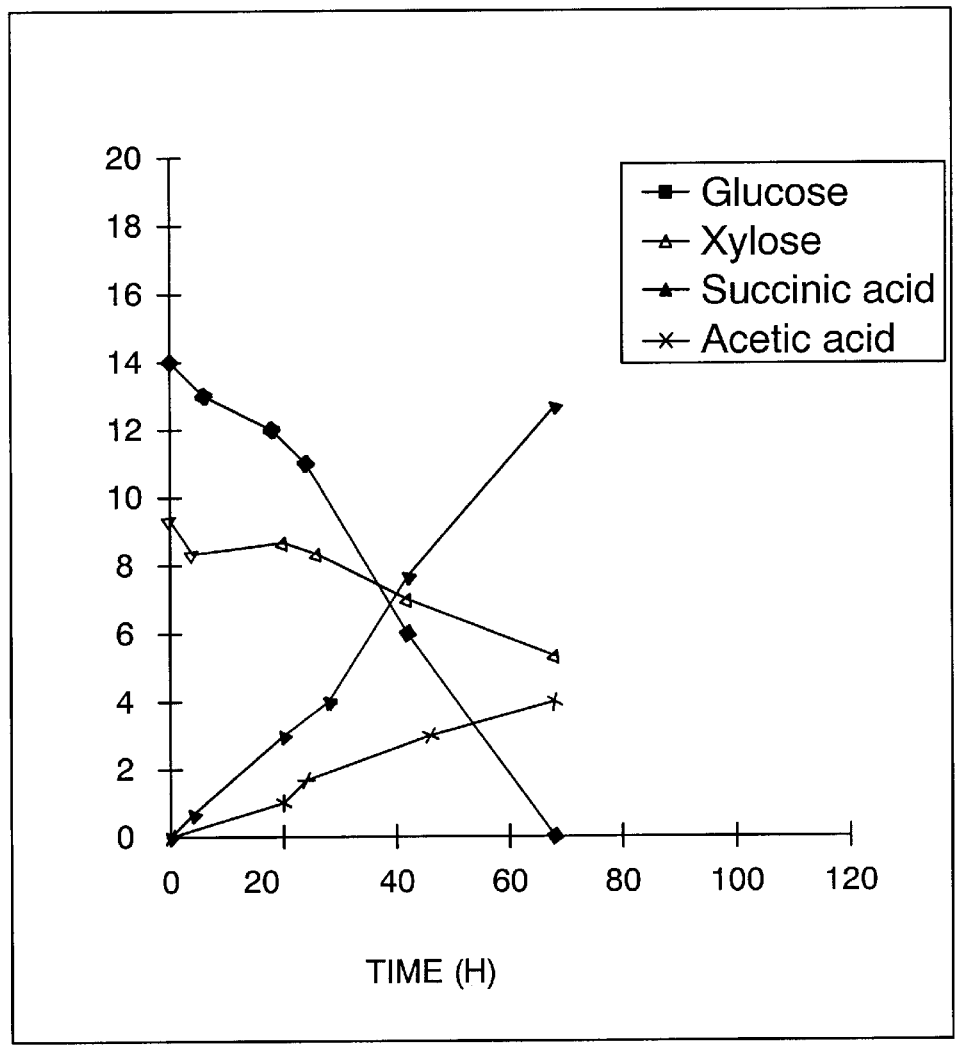
FIG. 3 is a graph depicting co-metabolism of a natural mutant bacteria, in accordance with features of the present invention.

The inventors also have found that the mutant confers upon transformed bacteria the ability to simultaneously utilize glucose and non-glucose sugars to produce succinic acid. FIG. 3 illustrates how the natural mutant containing the ptsG mutation, metabolizes glucose and xylose to produce succinic acid. The data shows that 14 grams per liter (g/L) of glucose produces approximately 10 g/L of succinic acid. As such, the data confirm that xylose also is being metabolized to produce the additionally detected succinic acid to arrive at a peak succinic acid concentration of approximately 15 g/L.

Inasmuch as a single intact ptsG gene confers catabolite repression, transformation of target bacteria with the ptsG mutation must effect an homologous recombination with the recipient chromosome. Transduction of the bacteria using phage is therefore most suitable. However, alternative methods of introduction of the mutant gene are available, including the use of suicide plasmids. Details of the transduction are provided infra.

Growth Detail

E. coli strains suitable for transformation are listed on Table 1, supra. Initially, the strains are cultured in Luria Bertani medium at 37° C. Antibiotics were included as necessary at the following concentrations: 100 μg of ampicillin per ml, 30 μg of kanamycin per ml, 10 μg of tetracycline per ml, and 30 μg of chloramphenicol per ml. Rich broth contained (per liter), 10 g of tryptone, 5 g of NaCl, and 1 g of yeast extract. Solid media for plates contained 1.5 percent (wt/vol) Difco Bacto-Agar. Minimal medium E was prepared as described in Vogel, H. J. 1956 *Acetylornithinase in E. coli,. Biol. Chem.* 218:97–103, and incorporated herein by reference.

Fermentative growth was performed in sealed serum tubes containing 10 ml of LB medium, supplemented with 0.5 g of MgCO$_3$ (added in order to maintain the pH of the medium during fermentation), antibiotics, and approximately 10 g/L of glucose. A myriad of growth substrates can be utilized, including but not limited to sugars, sugar alcohols, sugar acids and combinations thereof. The following sugars were tested in place of glucose at a concentration of 5 g/L in anaerobic growth: trehalose, mannose, fructose, sorbitol, and glucuronic acid.

Inocula for the anaerobic liquid cultures were prepared by growing the strains aerobically overnight in LB medium supplemented with antibiotic. A sample of the overnight culture was diluted 100-fold in fresh media and allowed to grow aerobically to an A$_{600}$ of approximately 2; the anaerobic growth media was inoculated with 2 ml of the inocula.

TABLE 3

Expression of the alternate succinic acid-producing pathway in strains of the W1485 lineage

| Strains | Source | Catabolite repression[a] | Glucose remaining and products formed (g/L)[b] | | | | | |
|---|---|---|---|---|---|---|---|---|
| | | | Glucose | SA | AA | FA | LA | EtOH | Pyruvate |
| W1485 | wild type | + | 0.00 | 1.99 | 3.51 | 3.10 | 0.79 | 2.93 | 0.001 |
| AFP165 | P1 (RC308) X W1485 | – | 0.52 | 6.45 | 2.79 | 1.15 | 0.00 | 2.25 | 0.000 |
| FMJ123 | W1485, pfl::Cam | + | 0.00 | 1.09 | 0.54 | 0.16 | 11.47 | 0.20 | 0.003 |
| AFP166 | P1 (RC308) X FMJ123 | – | 0.40 | 7.86 | 2.49 | 0.26 | 0.38 | 1.57 | 0.003 |
| LS1 | W1485, ldh::Kan | + | 0.00 | 1.97 | 3.83 | 2.89 | 0.47 | 2.98 | 0.002 |
| AFP167 | P1 (RC308) X LS1 | – | 0.00 | 7.39 | 2.16 | 0.83 | 0.00 | 2.46 | 0.000 |
| NZN111 | W1485, pfl::Cam, ldh::Kan | + | 10.03 | 0.08 | 0.96 | 0.64 | 0.07 | 0.19 | 0.177 |
| AFP111 | NZN111, afp=ptsG | – | 0.00 | 7.46 | 2.12 | 0.51 | 0.25 | 2.29 | 0.003 |

[a]The presence or absence of catabolite repression, depicted by (+) or (–), respectively, was determined by the coloration of individual colonies on X-gal-containing agar.
[b]Fermentative growth of strains and quantitation of products formed is described under "Growth Detail." SA = succinic acid, AA = acetic acid, FA = formic acid, LA = lactic acid and EtOH = ethanol. Thirteen g/L of glucose was included in the media; glucose remaining and products formed were quantitated following 28 hours of anaerobic growth.

Samples were removed anoxically from the sealed tubes at appropriate times for analysis of levels of glucose (or alternate sugar substrates) remaining and fermentation products formed. For anaerobic growth on solid media, agar plates were incubated at 37 C in an anaerobic jar under an H2—CO2 atmosphere generated by use of a Gas-Pak.

A plate assay for β-galactosidase activity was used to test for the presence of normal catabolite repression in strains.

LB or Medium E-agar are two of several mediums which can be utilized. Medium E-agar is a minimum-nutrient medium commonly used, and discussed in Vogel, H. J., 1956 *Acetylornithase in E. coli, J. Bio/Chem* 218:97–103 and incorporated herein by reference. In exemplary protocols, LB or Medium E-agar is supplemented with 4 g/L of glucose, 4 g/L of lactose, 3 mg/L of 5-bromo-4-chloro-3-indolyl-β-D-galactoside (X-gal), and antibiotics. These media are hereinafter referred to as X-gal/glucose agar. The formation of blue colonies indicated expression of β-galactosidase in the presence of glucose due to the absence of normal catabolite repression. Conversely, the formation of white colonies indicated that normal catabolite repression existed, and therefore no enzyme was present to cleave the disaccharide lactose.

Mutant Mapping Detail

High Frequency of Recombination (Hfr) conjugations for mapping of the ptsG gene mutation were performed using the set of Hfr donor strains disclosed in Wanner, B. L. 1986 *Novel Regulatory Mutants of the Phosphate Regulon in E. coli. J of Mol. Biol.* 191: 39–59, and incorporated herein by reference. AFP 111 was used as the recipient, and 15–20-minute mating periods were typically allowed. Exconjugants were selected for resistance to tetracycline (to select for the transfer of the Tn 10 into the recipient) and kanamycin (to select against the donor), and screened for the formation of white colonies on LB-agar claims containing X-gal (described above) to indicate the transfer of a locus that restored normal catabolite repression in the recipient AFP 111. Exconjugant colonies were purified by restreaking on the same selective medium; well isolated white colonies were chosen for analysis of fermentative metabolism.

P1 phage transductions were carried out according to Miller, J. H. 1972 *Experiments in Molecular Genetics* Cold Spring Harbor Laboratory, Cold Spring Harbor, N.Y., and incorporated herein by reference. AFP 111 was used as the recipient, and transductants were selected by the procedure described for the exconjugants, with the exception that medium E-agar plates were used in place of LB-agar to prevent further lysis of the host by residual P1 phage.

To create a strain with a Tn 10 positioned near a defective ptsG gene zce, Tn10 was transduced from strain CAG 12078 into strain La-12G (CGSC #5085,ptssG21). LA-12G formed blue colonies on X-gal/glucose agar, confirming the expected lack of catabolite repression. Transductants from the (P1) CAG12078 X LA-12 cross were screened for resistance to tetracycline and the formation of blue colonies on X-gal/glucose agar (indicating transfer of the Tn 10 into La-12G without replacement of the ptsG21 allele). One such transductant, designated RC308, was subsequently used to transduce ptsG21 into various strains with normal catabolite repression. Transductants from these crosses were screened for resistance to tetracycline and for the formation of blue colonies on X-gal/glucose agar (indicating the loss of catabolite repression in the recipient)

Positive exconjugants were obtained with Hfr donor BW7623 (Table 4), indicating that the mutation was in the 10- to 30-minute region of the *E. coli* chromosome. Further experimentation revealed that the mutant resides at the 25 minute region of the genome. Seven positive exconjugants were analyzed for glucose fermentation and were observed to produce elevated levels of formic acid, low amounts of ethanol, and were observed to produce elevated levels of formic acid, low amounts of ethanol, and acetic and succinic acids. Succinic acid levels produced by the exconjugants were similar to levels observed for W1485. These data are consistent with the presence of functional pflAB genes and replacement of the afp mutation with the wild type allele in the exconjugants. The exconjugants were sensitive to chloramphenicol, suggesting that the formic acid produced was the result of functional pflAB genes having replaced the ΔpflAB::Cam of AFP111.

To map the afp mutation in greater detail, transductions were performed using P1 bacteriophage grown on a set of stains containing Tn 10 insertions close to the ptsG (24.96 min), ptsH (54.55 min), ptsI, (54,56 min), and crr (54.60 min) genes of the PTS. AFP111

TABLE 4

Frequencies from Hfr and P1 mapping studies

| Hfr or P1 donor strain | Position of Tn10 in donor strain (min) | Origin and direction of chromosome transfer by Hfr donor strain[a] | Frequency of cotransfer (%)[b] |
|---|---|---|---|
| BW7623 (Hfr) | 11.9 | 32 min, CCW | 14.0 |
| BW6156 (Hfr) | 94.2 | 7 min, CCW | 0 |
| BW6159 (Hfr) | 85.1 | 68 min, CW | 0 |
| CAG12078 (P1) | 24.6 | — | 86.4 |
| CAG18463 (P1) | 25.5 | — | 12.5 |
| CAG18468 (P1) | 54.1 | — | 0 |
| CAG18470 (P1) | 55.7 | — | 0 |

[a]CCW and CW denote counterclockwise and clockwise, respectively.
[b]Frequencies shown are for exconjugants or transductants that formed white colonies on X-gal-containing agar (medium defined under "Materials and Methods") and were resistant to both tetracycline and kanamycin.

was used as the recipient, and transductants were selected in a manner similar to that described for exconjugants. Cotransduction frequencies of 86.4% and 12.5% were obtained with P1 donor strains CAG12078 (Tn10 at 24.6 min) and CAG18463 (Tn10 at 25.5 min), respectively (Table 4), suggesting that the ptsG locus contained the mutant.

Glucose consumption and product formation during fermentation was quantitated by high performance liquid chromatography ion exchange column. Glucose levels were also monitored enzymatically. Pyruvate levels were determined enzymatically.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for changing fermentative bacteria to succinic acid producing bacteria comprising:
   a) selecting a bacterial strain having a phosphotransferase system; and
   b) altering the phosphotransferase system so as to allow the bacterial strain to simultaneously metabolize different sugars, wherein the alteration of said phosphotransferase system involves homologous recombination of a defective ptsG gene from strain LA-12G.

2. The method as recited in claim 1 wherein the bacteria are selected from the group consisting of *E. coli* Klebsiella, Erwinia, and Lactobacillus.

3. The method as recited in claim 1 wherein the step of altering the phosphotransferase system further includes the step of homologously recombining the defective phosphotransferase gene with a portion of the bacteria's chromosome.

4. The method as recited in claim 3 wherein the recombination occurs via phage transduction.

5. The method as recited in claim 1 wherein the sugars are selected from the group consisting of glucose, sorbitol, xylose, arabinose, mannose, lactose, glucuronic acid, and combinations thereof.

6. A method for increasing succinic acid production in a bacterium, comprising:
   a) selecting a bacteria having a phosphotransferase system containing a ptsG gene;
   b) creating a mutation in the ptsG gene which allows the bacteria to metabolize sugars other than glucose in the presence of glucose; and
   c) selecting those bacteria with increased succinic acid production.

7. The method as recited in claim 6 wherein the bacteria are selected from the group consisting of *E. coli,* Klebsiella, Erwinia, and Lactobacillus.

8. The method as recited in claim 6 wherein the sugar is selected from the group consisting of glucose, sorbitol, xylose, arabinose, mannose, lactose, glucuronic acid, and combinations thereof.

9. The method as recited in claim 7 wherein the ptsG mutation resides in the 10–30 minute region of the *E. coli* chromosome.

* * * * *